(12) United States Patent
Pavlov et al.

(10) Patent No.: US 10,531,958 B2
(45) Date of Patent: Jan. 14, 2020

(54) IMPLANT ASSEMBLY FOR THE SACROILIAC JOINT

(71) Applicants: RIOS MEDICAL AG, Stans (CH); IGNITE-CONCEPTS GMBH, Langendorf (CH)

(72) Inventors: Paul Pavlov, Nijmegen (NL); Tom Overes, Langendorf (CH)

(73) Assignees: RIOS MEDICAL AG, Stans (CH); IGNITE-CONCEPTS GMBH, Langendorf (CH)

( * ) Notice: Subject to any disclaimer, the term of this patent is extended or adjusted under 35 U.S.C. 154(b) by 249 days.

(21) Appl. No.: 15/523,387

(22) PCT Filed: Mar. 16, 2015

(86) PCT No.: PCT/CH2015/000043
§ 371 (c)(1),
(2) Date: Apr. 29, 2017

(87) PCT Pub. No.: WO2016/065489
PCT Pub. Date: May 6, 2016

(65) Prior Publication Data
US 2017/0246000 A1 Aug. 31, 2017

(30) Foreign Application Priority Data
Oct. 31, 2014 (CH) ........................ 1674/14

(51) Int. Cl.
*A61F 2/44* (2006.01)
*A61F 2/30* (2006.01)
(Continued)

(52) U.S. Cl.
CPC ...... *A61F 2/30988* (2013.01); *A61B 17/7055* (2013.01); *A61B 17/7082* (2013.01);
(Continued)

(58) Field of Classification Search
CPC .................. A61B 17/7055–17/7059; A61B 17/80–17/8095; A61F 2002/30995
See application file for complete search history.

(56) References Cited

U.S. PATENT DOCUMENTS 2,964,152 A * 12/1960 Banner ................. B23P 19/069
192/48.611
6,227,782 B1 * 5/2001 Bowling ............... F16B 35/048
411/114
(Continued)

FOREIGN PATENT DOCUMENTS

WO 2012/174485 A1 12/2012

*Primary Examiner* — Nicholas J Plionis
*Assistant Examiner* — Steven J Cotroneo
(74) *Attorney, Agent, or Firm* — Maschoff Brennan

(57) ABSTRACT

The present application relates to an implant system, preferably for the sacroiliac joint, comprising an implant body with at least two adjacent apertures, at least two screws and an insertion instrument assembly. Each screw comprises a screw head and a threaded elongated shaft. The at least two screws are rotatably engaged within said at least two apertures. The insertion instrument assembly includes a basis, a first holding means and at least one rotatable driving means configured for engagement with a drive of at least one of said at least two screws. The at least two screws or said insertion instrument assembly comprises transmission means such that a rotational movement of a first screw of said at least two screws is transferred to the at least one further screw.

14 Claims, 14 Drawing Sheets

(51) Int. Cl.
*A61B 17/70* (2006.01)
*A61F 2/46* (2006.01)

(52) U.S. Cl.
CPC .......... *A61F 2/4425* (2013.01); *A61F 2/4611* (2013.01); *A61F 2002/30995* (2013.01)

(56) References Cited

U.S. PATENT DOCUMENTS

| | | | | |
|---|---|---|---|---|
| 6,253,644 B1* | 7/2001 | Duquette | ............. | B23P 19/069 81/57 |
| 6,543,314 B1* | 4/2003 | Hoyt | .................... | B23P 19/069 74/397 |
| 7,704,279 B2* | 4/2010 | Moskowitz | ........ | A61B 17/0642 623/17.11 |
| 7,731,721 B2* | 6/2010 | Rathbun | ............ | A61B 17/1728 606/87 |
| 7,846,188 B2* | 12/2010 | Moskowitz | ........ | A61B 17/0642 606/279 |
| 7,971,509 B2* | 7/2011 | Shortridge | ............ | B25B 15/007 81/57.22 |
| 8,172,854 B2* | 5/2012 | Blain | ................. | A61B 17/1728 606/86 A |
| 8,381,619 B2* | 2/2013 | Hung | .................... | B25B 17/02 81/57.22 |
| 8,740,983 B1 | 3/2014 | Arnold et al. | | |
| 9,179,951 B2* | 11/2015 | Suh | ........................ | A61B 17/56 |
| 9,421,109 B2* | 8/2016 | Donner | ................. | A61B 17/68 |
| 10,052,142 B2* | 8/2018 | Biedermann | ...... | A61B 17/8057 |
| 2008/0021454 A1* | 1/2008 | Chao | ................... | A61B 17/7044 606/250 |
| 2008/0033440 A1* | 2/2008 | Moskowitz | ........ | A61B 17/0642 606/251 |
| 2008/0103601 A1 | 5/2008 | Biro et al. | | |
| 2010/0145397 A1 | 6/2010 | Overes et al. | | |
| 2011/0238181 A1* | 9/2011 | Trieu | ................. | A61B 17/1735 623/17.11 |
| 2012/0022595 A1* | 1/2012 | Pham | ................. | A61B 17/7032 606/278 |
| 2013/0018427 A1 | 1/2013 | Pham et al. | | |
| 2013/0053966 A1 | 2/2013 | Jimenez et al. | | |
| 2013/0103156 A1 | 4/2013 | Packer et al. | | |
| 2014/0135927 A1* | 5/2014 | Pavlov | .............. | A61B 17/7055 623/17.11 |
| 2014/0142700 A1* | 5/2014 | Donner | ..................... | A61F 2/44 623/17.11 |
| 2014/0163683 A1* | 6/2014 | Seifert | .................. | A61F 2/4425 623/17.15 |
| 2014/0276891 A1* | 9/2014 | Defalco | ............. | A61B 17/8875 606/104 |
| 2015/0265321 A1* | 9/2015 | Perry | .................... | A61F 2/4455 606/86 A |
| 2016/0157897 A1* | 6/2016 | Vaidya | ............... | A61B 17/7059 606/279 |
| 2017/0246000 A1* | 8/2017 | Pavlov | ............... | A61F 2/30988 |
| 2017/0296344 A1* | 10/2017 | Souza | ....................... | A61F 2/28 |
| 2018/0014939 A1* | 1/2018 | Arnold | .............. | A61B 17/8066 |

* cited by examiner

IMPLANT ASSEMBLY FOR THE SACROILIAC JOINT

TECHNICAL FIELD

The invention relates to an implant assembly for the sacroiliac joint which provides a high stability and which is minimally invasive.

BACKGROUND ART

Lower back pain is a common type of pain in adults. There are many different causes of lower back-pain, such as degenerated discs having lost height hence causing nerve roots to be compressed between the vertebral bodies, or herniated nucleus portions pressing against nerves. However, in about 15% of the cases lower back pain is caused by irritation or inflammation of the sacroiliac joint (SI-joint). This joint connects the hip bones to the spinal column. In a first variant, lower back pain caused by the SI-joint is treated by non-surgical treatment, such as physical therapy, chiropractic manipulations, oral medications, injection therapy or intermittent use of a pelvic belt for symptomatic relief.

If a patient does not respond to conservative treatment, fusion of the SI joint is an option to eliminate the pain. To achieve fusion an implant is placed in the joint or across the joint, restraining the painful motion and causing both joint surfaces to grow together.

The SI-joint is characterised by being very irregular and having a three dimensionally curved joint surface. Furthermore, the bones being connected by the SI-joint, the ilium bone and the sacral bone, have very different bone quality. The ilium bone is much harder than the sacral bone. At the joint surface, both bones can be considered having substantially equal strength and rigidness. The combination of the shape and quality provides challenges for the implantation procedure and implant design.

Currently, a number of implant systems and techniques exist. One fusion technique is to screw multiple screws from the lateral side through the ilium bone into the sacral bone. The screws stabilize and compress the joint surfaces together, causing both bones to fusion over time. In an alternative technique porous elongated spacers are placed into the joint, promoting the fusion of the bones. However, placing such devices and screws bears a risk of damaging nerves that are located close to the sacral bone. These techniques are called lateral approach to the joint.

Another surgical approach to the joint is the posterior approach. In this technique, the joint is treated by entering from the posterior side or back-side of the joint. A large, conical and self-cutting hollow screw is placed between and through the joint surfaces. The screw cuts away and into the highly irregular curved, but stable joint surfaces, hence sinking into the bones and causing the joint to fuse. This approach is safe and stays away of neurovascular structures.

WO 2012/174485 (JCBD LLC) discloses a sacroiliac joint implant system having an elongated body and at least one fixation member or a pair of fixation members which extend outward from the longitudinal axis of an implant body. The implant system comprises a delivery tool having an implant body retainer including a drive shaft and implant body engagement shafts which are rotatably supported in a frame. The drive shaft is rotatably supported within the frame and comprises a geared portion engaged via a geared relationship with geared proximal ends of the engagement shafts such that a rotation of the drive shaft entails a rotation of the engagement shafts. Rotation of said engagement shafts allows threaded ends of the engagement shafts to be threadably received in threaded bores of the implant body such as to secure the implant body to the delivery tool.

SUMMARY OF THE INVENTION

It is the object of the invention to create an implant and implant system for sacroiliac interference procedures which provide a high stability and which are less invasive.

The solutions of the invention are specified by the features of claims 1 and 11. According to the invention, the implant system comprises an implant body with at least two adjacent apertures and at least two screws, each screw having a screw head and a threaded elongated shaft, said at least two screws being rotatably engaged within said at least two apertures. Further, the implant system includes an insertion instrument assembly with a basis, a first holding means and at least one rotatable driving means. The at least one rotatable driving means is configured for engagement with a drive of at least one of said at least two screws. Said at least two screws or said insertion instrument assembly comprise a transmission means such that a rotational movement of a first screw of said at least two screws is transferred to the at least one further screw.

The inventive implant assembly has the advantage that the screws used to fixate the implant body, e.g. within the sacroiliac joint, are rotated simultaneously. Hence, the screws advance in a synchronous manner into the joint space between the ilium and the sacral bone. Further, the implant body will likewise be advanced into the joint space in a regular and even manner.

Preferably, said implant body has a generally rectangular shape with rounded edges. The at least two adjacent apertures are preferably arranged along a length axis of said implant body. The number of apertures corresponds to the number of screws.

The term "adjacent" as understood herein means that the at least two apertures are arranged on said implant body at a relatively short distance from each other. In certain special embodiments, the at least two apertures are positioned so close that the screw heads of the at least two screws touch each other.

Preferably, the central axes of the at least two apertures are arranged parallel to each other and along a straight line. For example, in the case that the implant system comprises more than two apertures, the central axes of all apertures are all arranged along a straight line relative to each other, i.e. all central axes are comprised on an imaginary plane.

In a preferred embodiment, said implant system comprises more than two screws, most preferably three screws. Accordingly, the implant body comprises more than two apertures, most preferably three apertures.

The screws are rotatably engaged within said apertures by means of the screw heads. The threaded elongated shafts of the at least two screws are protruding from said implant body on the same side. Preferably, said treaded elongated shafts of said at least two screws have the same length and each comprises a thread having the same thread pitch. The at least two apertures are configured to comprise a blocking surface which may engage with the screw head such as to provide a contact surface between the implant body and the screws. With such a configuration the screws may be used to advance and secure the implant body within the sacroiliac joint by means of the screws.

Preferably, the screw heads of the at least two screws are rotatably engaged within said at least two apertures in an inseparable manner, i.e. the screw heads may not be removed from said apertures without application of a considerable amount of force. For example, the screw heads may be hold within the at least two adjacent apertures in a form-fitting manner. This may be achieved by providing constriction elements in said at least two apertures which lock the screw heads in a defined position within the apertures, e.g. between the stopping surface and the constriction element. In order to be able to insert the screws into the apertures, the screw heads may comprise resilient structures which allow a unidirectional passage across the constriction element into the defined position.

The first holding means are preferably configured to provide an ergonomic grip, e.g. for a surgeon. The first holding means most preferably is in the form of a handle. The basis of the insertion instrument assembly connects the first holding means with the rotatable driving means.

The at least one rotatable driving means are preferably configured as shaft being rotatably coupled with the basis, e.g. by being inserted in a channel provided in said basis. The rotatable driving means preferably comprise a male drive at one end, said male drive being releasably engagable with the at least one screw, e.g. by means of a mating female drive located on said screw head. At the other end, the shaft preferably comprises means for imparting a rotational torque, e.g. a knob or a coupling means for a power tool.

The transmission means may be located either on said insertion instrument assembly or said at least two screws. Preferably, said transmission means are in the form of a spur gear.

Alternatively, other means of transmission may be used, e.g. such as a transmission belt.

Preferably, at least one aperture is configured to be releasably connected with the insertion instrument assembly, preferably by means of an internal thread feature arranged in said at least one aperture and being connectable to a threaded end of said insertion instrument assembly.

With this arrangement the implant body may be coupled to the insertion instrument assembly prior to the implantation procedure and easily released once the implantation procedure is terminated. By providing the connection means in one of the at least two apertures, no additional features to enable a connection between the implant body and the insertion instrument assembly is necessary. Further, a threaded connection has the advantage of being angle stable, such that the implant body will not pitch relative to the insertion instrument assembly.

Preferably, said threaded end is arranged on a cannulated shaft rotatably coupled to said basis, one rotatable driving means being releasably arranged within said cannulated shaft.

Provision of a rotatable shaft allows an easy connection and release of the insertion instrument assembly and the implant body, as not the entire insertion instrument assembly has to be rotated to threadably engage or disengage from the implant body, but only the cannulated shaft. Further, by provision of rotatable driving means which are releasably arranged within the rotatable cannulated shaft the screw engaged within the aperture comprising the internal thread feature may be rotated.

The insertion instrument assembly preferably comprises one rotatable driving means for each of said at least two screws, wherein each of said rotatable driving means comprises a cogwheel shaped portion, said cogwheel shaped portions meshing with each other such as to transmit a rotational torque of one of said rotatable driving means to the at least one further rotatable driving means.

Preferably, said rotatable driving means are in the shape of rods comprising a male drive at a first end for coupling with mating female drives arranged on the screw heads of said at least two screws. The cogwheel shaped portions are preferably arranged on a second end of said rods. The cogwheel portions mesh with each other. Preferably, the cogwheel portions all comprise the same amount of teeth and have the same pitch circle circumference. Hence, any transmission of torque between the cogwheel portions will have a gear ratio of 1, i.e. no reduction or increase of the rotational speed or torque is present between the cogwheel shaped portions.

It is understood that due to the transmission neighbouring rods will have opposite directions of rotation. As a consequence, neighbouring screws will be imparted with opposite rotational movements.

In a preferred alternative embodiment, the screw heads of said at least two screws each comprise a toothed circumference. The teeth of said toothed circumferences mesh with each other such that a rotational movement of one of said screws is transmitted to the at least one further screw.

The screw heads of the at least two screw act as spur gear such as to transmission rotational torque and movement between the screws. This has the advantage that the insertion instrument assembly only needs to include on rotatable driving means, as any rotation and torque transmitted by the rotatable driving means onto said one screw will be transmitted via the screw head spur gear to the other screws.

Preferably, the toothed circumferences all comprise the same amount of teeth and have the same pitch circle circumference. Hence, any transmission of torque between the toothed circumferences will have a gear ratio of 1, i.e. no reduction or increase of the rotational speed or torque is present between the cogwheel shaped portions.

It is understood that due to the transmission neighbouring screws will have opposite directions of rotation.

Preferably, the ratio between a first thread lead of the threaded elongated shaft of a first screw and a second thread lead of the threaded elongated shaft of the at least one further screw neighbouring said first screw is equal to the ratio between a first diameter of the toothed circumference of the first screw and a second diameter of the toothed circumference of the at least one further screw.

In the case where neighbouring screws have different diameters of their toothed circumference, the gear ratio would not be equal to 1, but one of the screws would have a higher rotational speed than the other. This would lead to different advancement speeds into the joint space of the screws. Provision of different leads for the threads located on the threaded elongated shafts allows neutralizing this difference in screw advancement.

Hence, although the neighbouring screws have different diameters of their toothed circumferences, the threaded screw shafts will have the same advancement speed into the joint space.

A "lead" in the present application is understood to define the axial advancement of a screw shaft during one complete turn of 360°, i.e. the axial travel of the screw shaft for a single revolution of the screw.

Preferably, at least one aperture is configured to allow the screw engaged therein to swivel relative to a central axis of said aperture, preferably by a maximal angle in the range of 1° to 45°. Said at least one aperture preferably comprises at least one section with a spherical shape which allows rotation of the screw head along two additional rotational axes, such that the screw and hence the threaded elongated shaft may be arranged at any desired angle relative to the central axis of the aperture. The spherical shaped section thereby is configured such that a maximal angle is in the range of 1° to 45°, i.e. that the threaded elongated shaft of the screw has a maximal inclination from 1° to 45° in all directions relative to the central axis of the aperture.

Provision of such a configuration facilitates the implantation, as at least one screw may be oriented in a way which facilitates the implantation.

Preferably, the threaded elongated shaft of one of said at least two screws comprises a thread with a first handedness and in that the threaded elongated shaft of the further of said at least two screws comprises a thread with a second handedness being opposite of said first handedness. Hence, in the case where the transmission means are in the form of a spur gear, such as cogwheel shaped portions or toothed circumferences meshing with each other, the screws will have the same direction of advancement irrespective of their different direction of rotation. Preferably, in the case where the implant system comprises more than two screws, the threaded elongated shaft of each screw has a thread which has a handedness such that all screws will have the same direction of advancement upon rotation.

Other advantageous embodiments and combinations of features come out from the detailed description below and the totality of the claims.

BRIEF DESCRIPTION OF THE DRAWINGS

The drawings used to explain the embodiments show.

In the figures, the same components are given the same reference symbols.

PREFERRED EMBODIMENTS

Figure 1:
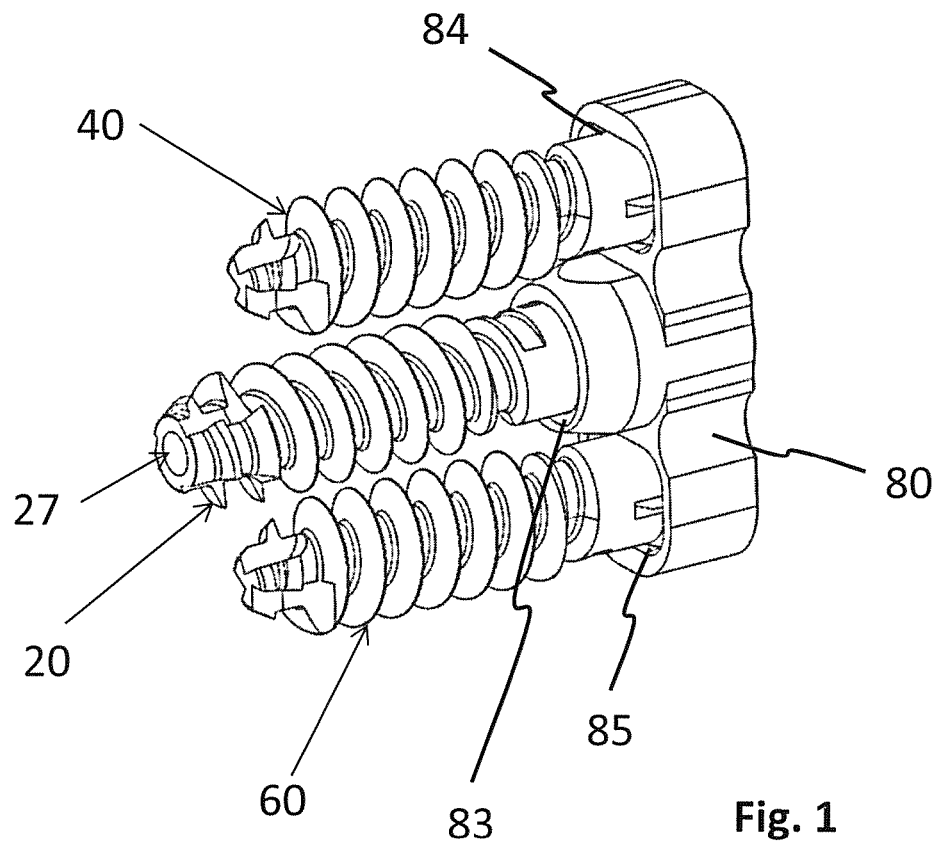
FIG. 1 a first embodiment of an implant body with three screws in a perspective view.

FIG. 1 shows a first embodiment of an implant body 80 in a perspective view. In this embodiment, the implant body 80 comprises three screws 20, 40, 60. Each of the screws 20, 40, 60 is arranged within an aperture 83, 84, 85 of the implant body 80. The first screw 83 comprises a first central cannulation 27 arranged along the central axis of the first screw 20, allowing the insertion of said first screw over a guide wire.

Figure 2A:
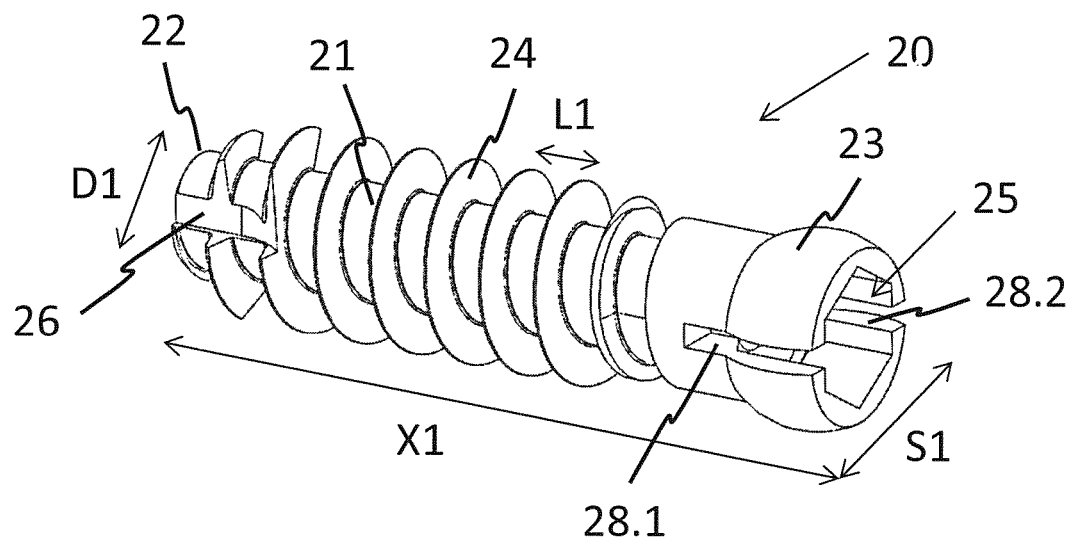
FIGS. 2a-2c detailed views of the different screws according to FIG. 1.
Figure 2B:
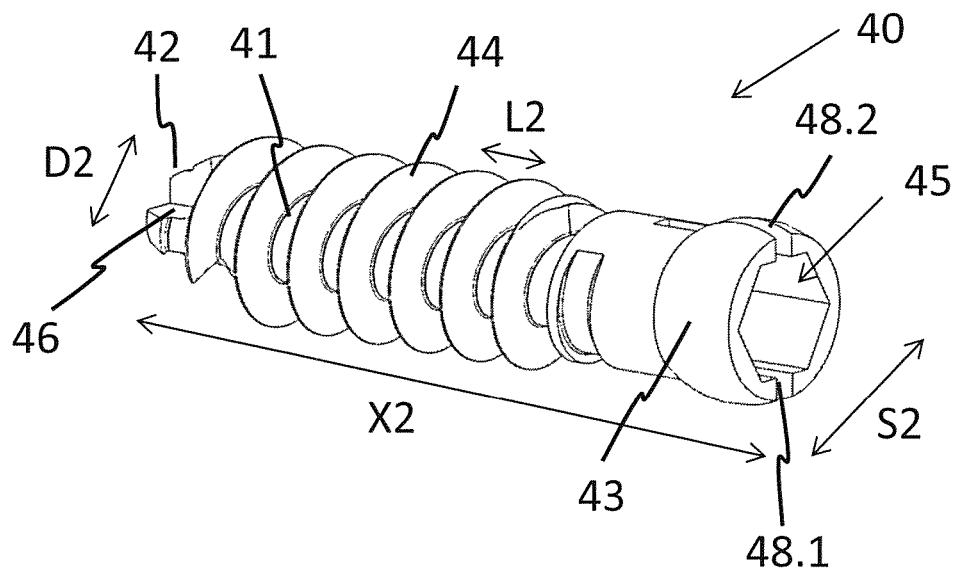
Figure 2C:
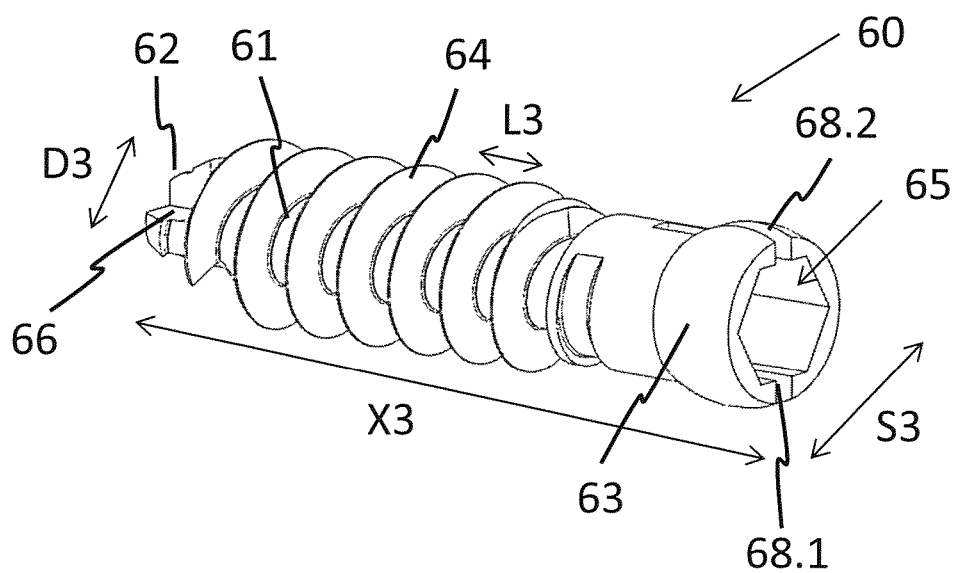

FIGS. 2a-2c show the different screws in greater detail. FIG. 2a is a representation of a first screw 20. The first screw 20 comprises a threaded first elongated shaft 21 which extends over a majority of the first length L1 of the first screw 20. The threaded first elongated shaft 21 has a first thread 25 with a first lead L1 and a first diameter D1. The first thread 24 is of a first handedness. At a first end, the first screw 20 comprises a first screw tip 22 and at a second, opposite end, the first screw 20 includes a first screw head 23. The first screw head has a first head diameter S1 which is larger than the first diameter D1 of the thread 24. Further, the first screw head 23 comprises a first female drive 25 as well as two first slots 28.1, 28.2. These two slots 28.1, 28.2 make the first screw head 23 resilient for assembly purposes.

A first cutting flute 26 is arranged at the first screw tip 22. The first cutting flute facilitates the advancement of the first screw 20 into the joint space without pre-drilling or pre-tapping.

FIG. 2b shows the second screw 40 in more detail. The second screw 40 comprises a threaded second elongated shaft 41 which extends over a majority of the second length L2 of the second screw 40. The threaded second elongated shaft 41 has a second thread 45 with a second lead L2 and a second diameter D2. The second thread 44 is of a second handedness. At a first end, the second screw 40 comprises a second screw tip 42 and at a second, opposite end, the second screw 40 includes a second screw head 43. The second screw head 43 has a second head diameter S2 which is larger than the second diameter D2 of the second thread 44. Further, the second screw head 43 comprises a second female drive 45 as well as two second slots 48.1, 48.2. These two second slots 48.1, 48.2 make the second screw head 43 resilient for assembly purposes.

A second cutting flute 46 is arranged at the second screw tip 42. The second cutting flute 46 facilitates the advancement of the second screw 40 into the joint space without pre-drilling or pre-tapping.

FIG. 2c shows the third screw 60 in more detail. The second screw 60 comprises a threaded third elongated shaft 61 which extends over a majority of the third length L3 of the second screw 60. The threaded third elongated shaft 61 has a third thread 65 with a third lead L3 and a third diameter D3. The third thread 64 is of the second handedness. At a first end, the third screw 60 comprises a third screw tip 62 and at a second, opposite end, the third screw 60 includes a third screw head 63. The third screw head 63 has a third head diameter S3 which is larger than the third diameter D3 of the third thread 64. Further, the third screw head 63 comprises a third female drive 65 as well as two third slots 68.1, 68.2. These two third slots 68.1, 68.2 make the third screw head 63 resilient for assembly purposes.

A third cutting flute 66 is arranged at the third screw tip 62. The third cutting flute 66 facilitates the advancement of the third screw 60 into the joint space without predrilling or pre-tapping.

Figure 3A:
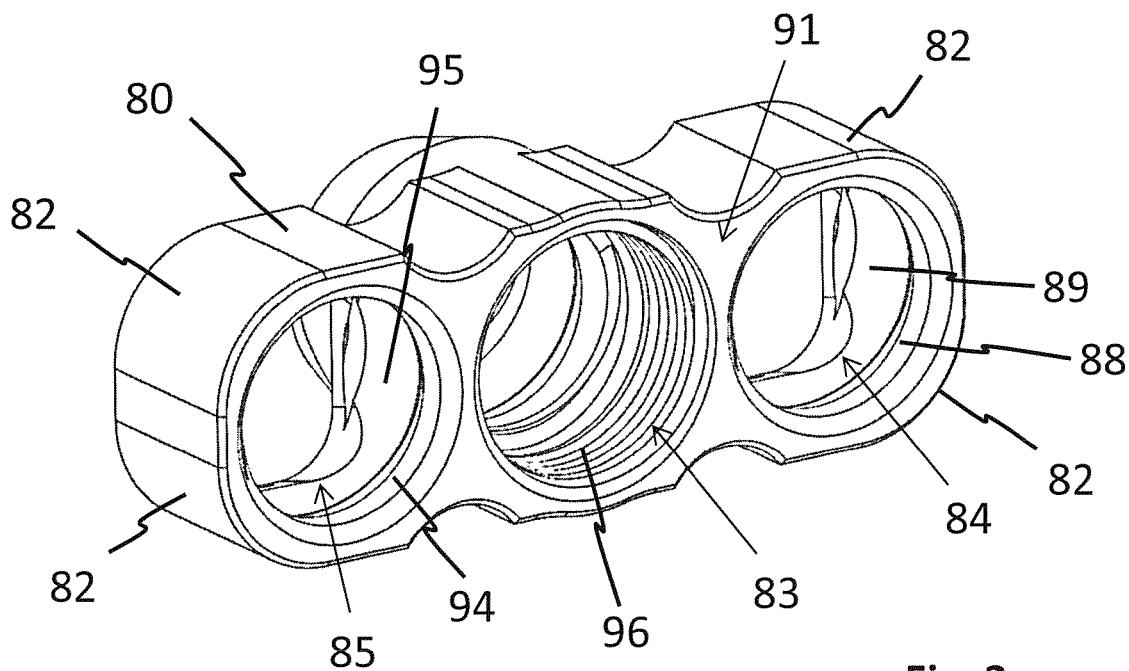
FIGS. 3a, 3b detailed views of the implant body.
Figure 3B:
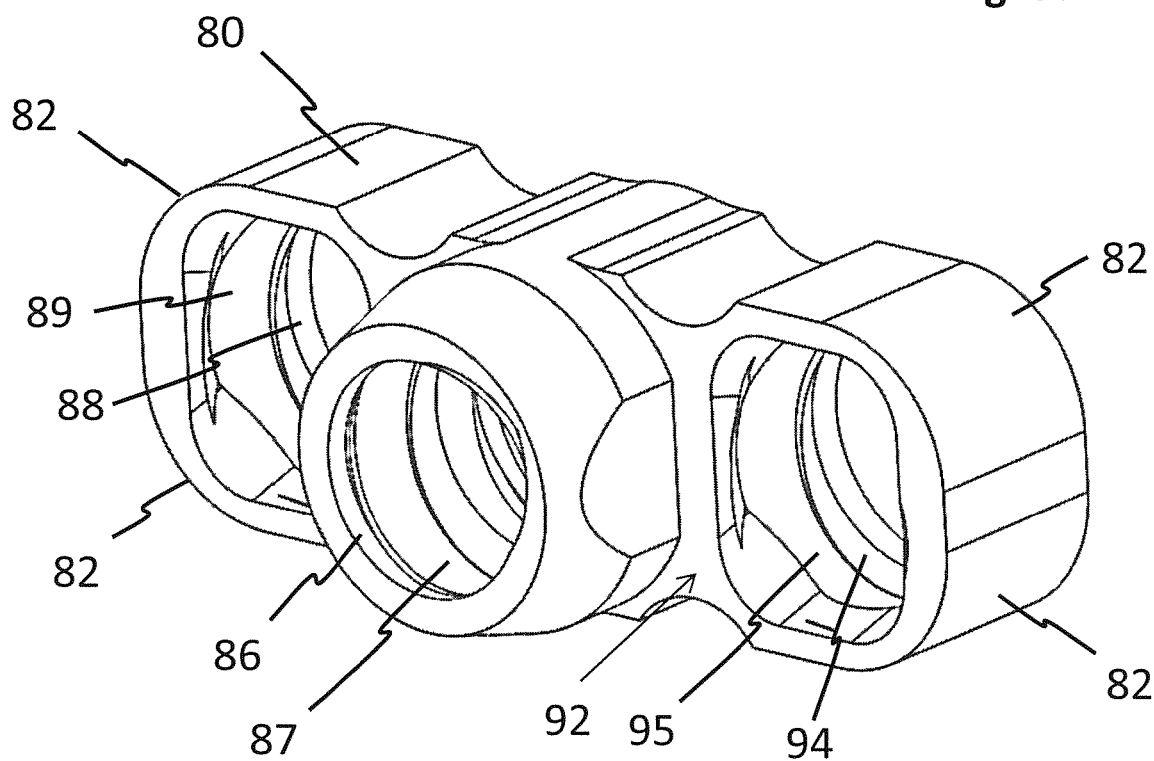

FIGS. 3a and 3b show said implant body 80 in greater detail. The implant body 80 features a front face 91 and a rear face 92. The implant body 80 is inserted into a joint space with the rear face 92 first, i.e. the front face 91 will be oriented towards a surgeon during the implantation procedure.

Preferably, the implant body 80 has rounded edges 82 to facilitate the insertion of the implant assembly 10 into a joint space.

Further, the implant body 80 comprises three apertures 83, 84, 85 which span from said front face 91 to said rear face 92. A first aperture 83 has a shape defined by a first cylindrical through bore 86 intersecting with a first spherical socket 87. A second aperture 84 and a third aperture 85 have a shape defined by a second cylindrical through bore 88 and a third cylindrical through bore 94, respectively, intersecting with a second spherical socket 89 and a third spherical socket 95, respectively. This defined shape of the apertures 83, 84, 85 allows the screw heads 23, 43, 63 of the screws 20, 40, 60 to swivel once engaged within said apertures 83, 84, 85.

By varying the shapes of the apertures different maximal swivel angles can be given to the screws 20, 40 and 60. Different swivel angles are needed for being compliant to the highly irregular curved shape of the joint surfaces.

Further, the first aperture 83 comprises an internal thread feature 96 for engagement with an insertion instrument assembly. Alternatively other attachment systems may be used for engaging the implant body 80 to an insertion instrument assembly, such as bayonet connections, external screw threads, snap-in features, magnetic connections, etc.

Figure 4A:
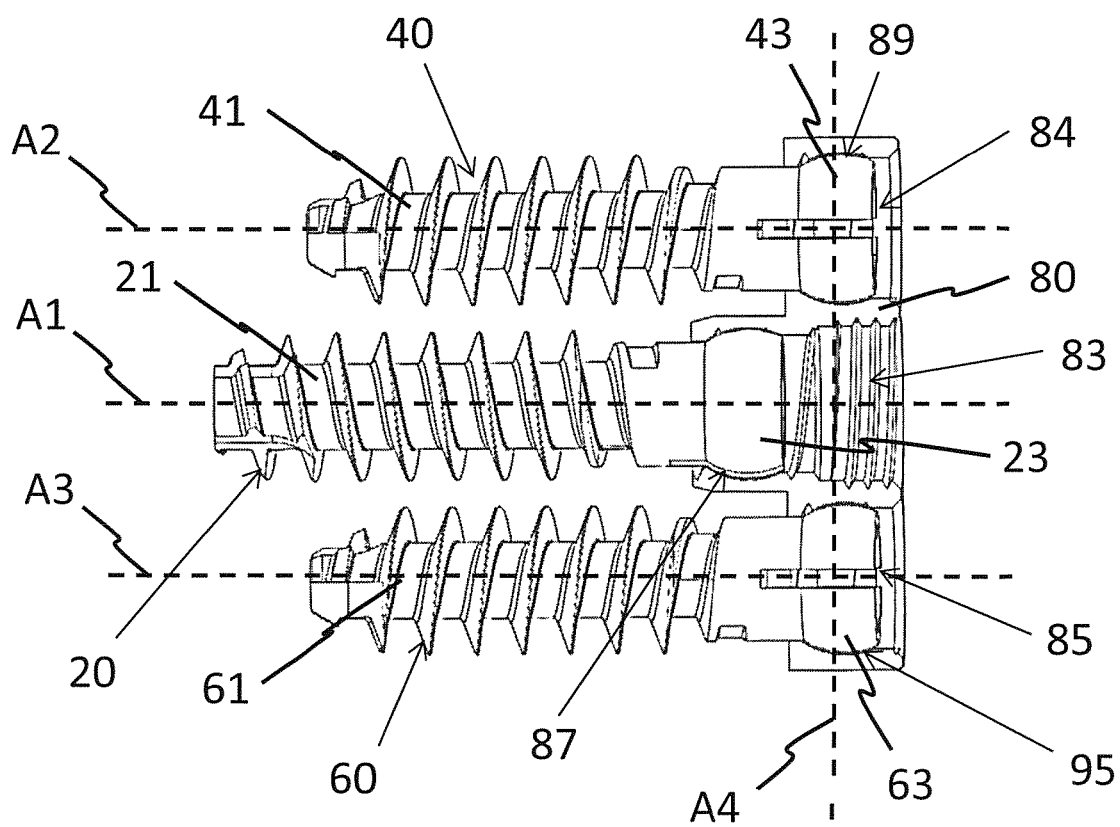
FIGS. 4a, 4b representations of the implant body in cross-sectional views.
Figure 4B:
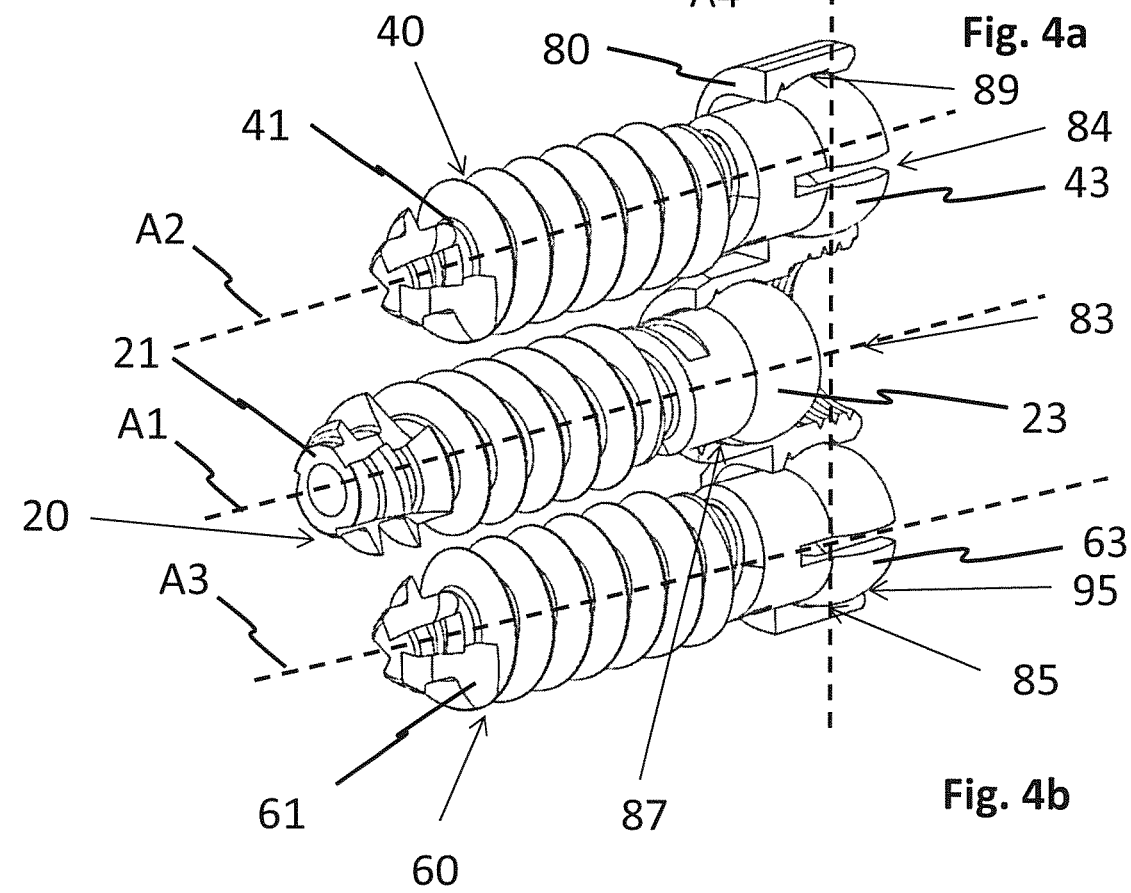

FIGS. 4*a* and 4*b* show the implant body 80 a cross-sectional view. The screws 20, 40, 60 are engaged within the apertures 83, 84, 85. As depicted, the first screw head 23 engaged within the first spherical socket 87, and the first threaded elongated shaft 21 is aligned with a first central axis A1 of said first aperture 83. In the embodiment shown, said first screw 20 has only one degree of freedom, namely rotation around the first central axis 'A1'.

The second screw head 43 is engaged within the second spherical socket 89, and the second threaded elongated shaft 41 is aligned with a second central axis A2 of the second aperture 84. In the embodiment shown, the second screw 40 has two degrees of freedom, namely axial rotation around the second central axis A2 and rotation around a fourth axis A4 being substantially perpendicular the central axes A1, A2, A3 and intersecting with the centre of said second screw head 43 and said third screw head 63.

Likewise, the third screw head 63 is engaged within the third spherical socket 95 and the third threaded elongated shaft 61 is aligned with a third central axis A3 of the third aperture 85. In the embodiment shown, the third screw 60 has two degrees of freedom, namely axial rotation around the third central axis A3 and rotation around the fourth axis A4.

In a preferred embodiment for assembly purposes, said screw heads 23, 43 and 63 comprise slots 28.1, 28.2, 48.1, 48.2, 68.1, 68.2. These slots 28.1, 28.2, 48.1, 48.2, 68.1, 68.2 allow the heads 23, 43, 63 to deflect when pressed inside said spherical sockets 87, 89, 95.

Alternatively, other elements may be used to engage the screws 20, 40, 60 in an inseparable manner. For example pins may be used, the implant body 80 could consist of a top part and a bottom part that are welded together after assembly, or the screws may consist of multiple parts being welded together.

Figure 5:
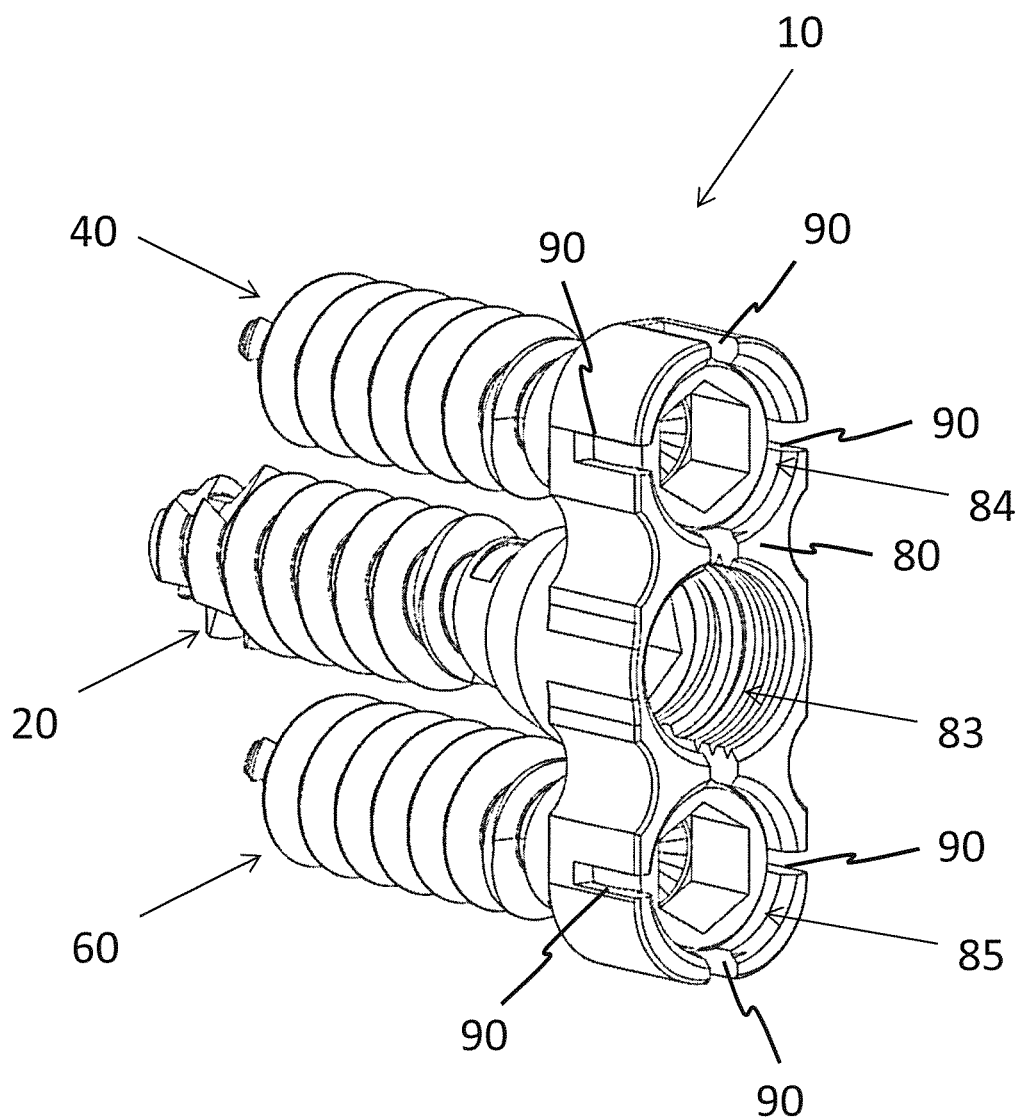
FIG. 5 a second embodiment of an implant body with three screws.

FIG. 5 shows a second embodiment of the implant body 80. In this embodiment, the walls of the apertures 83, 84, 85 comprise cut-outs 90. Said cut-outs 90 make the apertures 83, 84, 85 compliant such that screws 20, 40, 60 may be inserted into said apertures 83, 84, 85 more easily.

Figure 6:
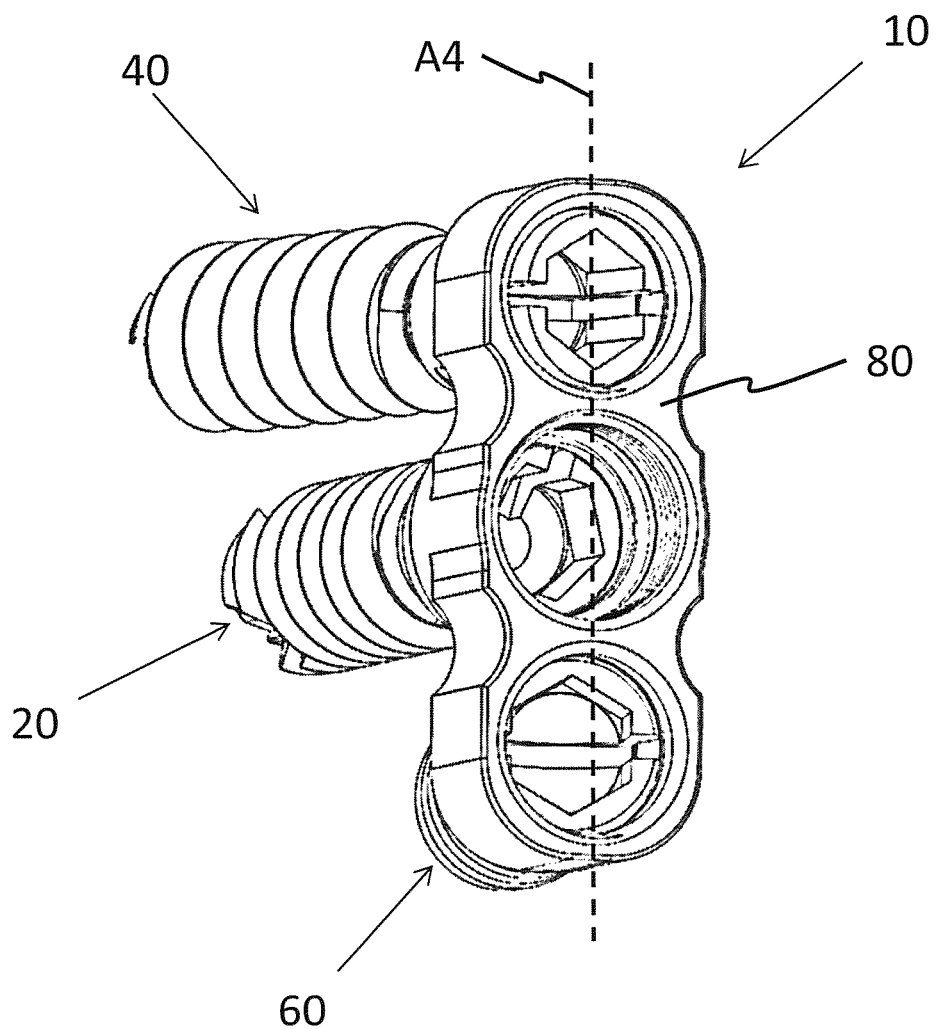
FIG. 6 the implant body according to FIG. 1 with a swiveled screw.

FIG. 6 shows the implant body 80 according to FIG. 1 with the second screw 40 and the third screw 60 swiveled around the fourth axis A4. As a result, each screw 40, 60 may be advanced forward in an individual direction.

Figure 7A:
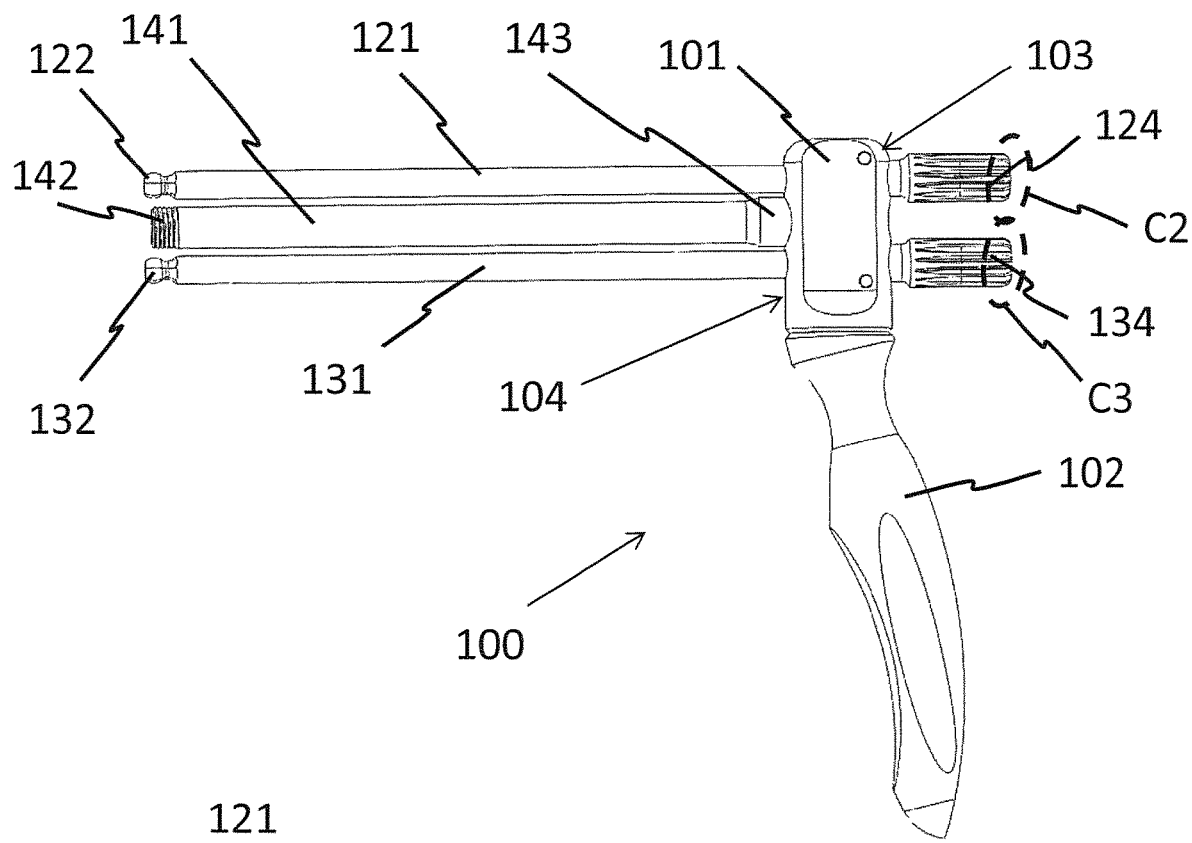
FIGS. 7a, 7b an embodiment of an insertion instrument assembly in a first configuration.
Figure 7B:
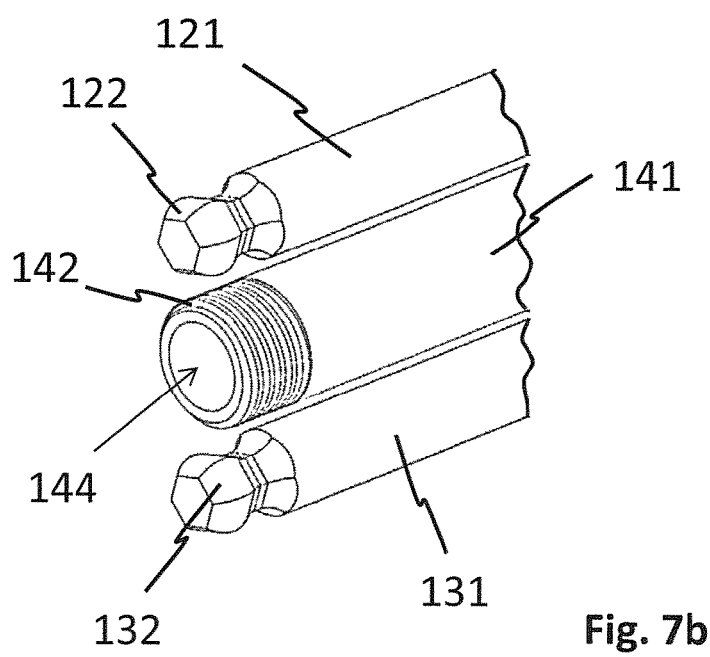

FIGS. 7*a* and 7*b* show the insertion instrument assembly 100 in a first configuration. FIG. 7*a* shows the insertion instrument assembly 100 as a side view, while FIG. 7*b* is a detail representation of a first end of said insertion instrument assembly 100.

The insertion instrument assembly 100 comprises a first handle 102, a basis 101 as well as a second rod 121 and a third rod 131 acting as driving means rotatably coupled to said basis 101.

Further, a cannulated shaft 141 acting as holding means is rotatably coupled to the basis 101. The basis 101 has a front side 103 and a rear side 104. The front side 103 will be oriented towards the surgeon during an implantation procedure.

The cannulated shaft 141 comprises a threaded end 142 configured for engagement with the internal thread feature 96 of said implant body 80. The cannulated shaft 141 includes a drive coupling 143 which may for example be coupled using with a hexagonal key such as to impart a rotational movement to the cannulated shaft 141. This allows threadingly engaging or disengaging said cannulated shaft 141 by means of the threaded end 142 with the internal thread feature 96. Furthermore, the cannulated shaft 141 has a cannulation 144.

The second rod 121 and the third rod 131 both comprise a male drive 122, 132, configured as a hexagonal drive in the example shown. In an alternative embodiment male drives 122, 132 may be a torx drive, a slotted drive, or any other drive able to transfer a rotational movement and a torque. In a preferred embodiment the male drives 122, 132 are configured as spherical drive geometry. Spherical drive geometries are known to be able to transfer torques without the need of being parallel to a screw axis.

Furthermore the second rod 121 comprises a second cogwheel portion 124. Said second cogwheel portion 124 has a second pitch circle circumference C2 and is located at the front side 103 of the basis 101.

Likewise the third rod 131 comprises a third cogwheel portion 134. Said third cogwheel portion 134 has a third pitch circle circumference C3 and is also located at the front side 103 of the basis 101.

Figure 8A:
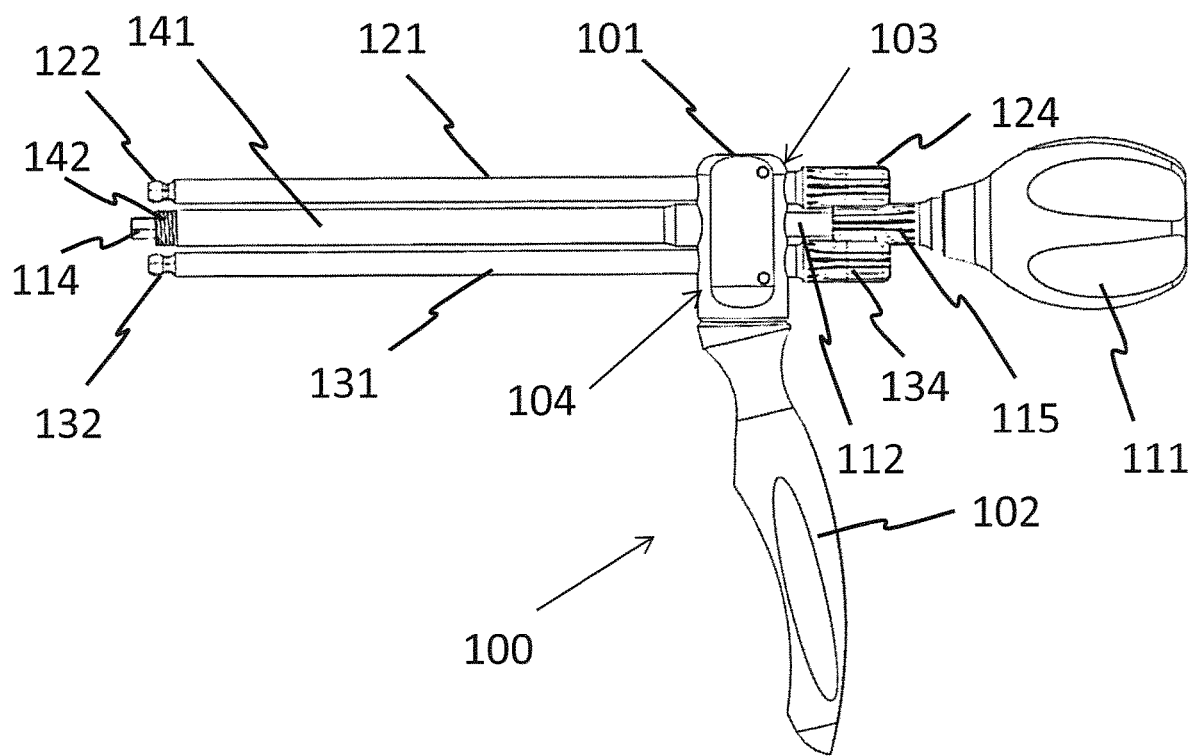
FIGS. 8a, 8b the insertion instrument assembly according to FIGS. 7a and 7b in a second configuration.
Figure 8B:
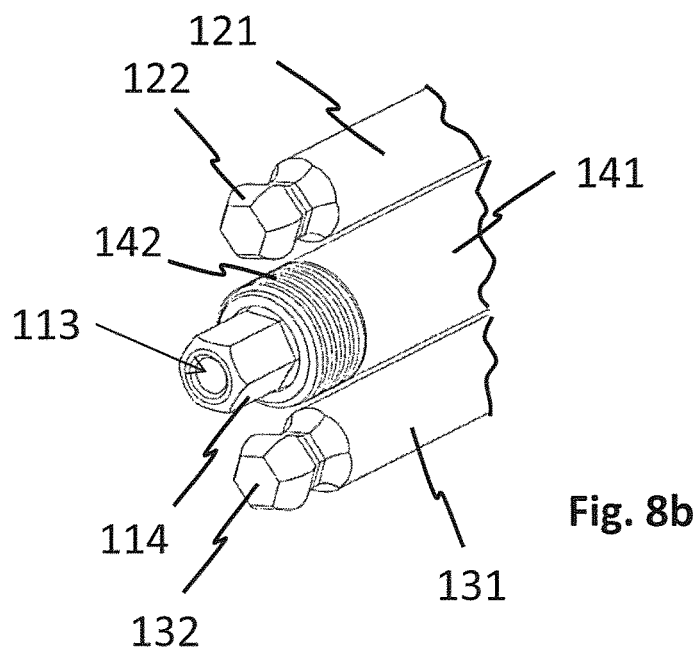

FIGS. 8*a* and 8*b* show the insertion instrument assembly 100 in a second configuration. In this second configuration, a first rod 112 is inserted within the cannulation 144 of the cannulated shaft 141. The first rod 112 acts as first rotation means. The first rod 112 comprises a first male drive 114 which will protrude from said cannulation 144 at the first end of the insertion instrument assembly 100. At a second end, the first rod 112 comprises a first cogwheel portion 115. By inserting the first rod 112 into said cannulation 144, the first cogwheel portion 115 meshes with said second cogwheel portion 124 and said third cogwheel portion 134. If a rotation and a torque are applied to said first rod 112, the rotation as well as the torque will be transmitted by means of the first cogwheel portion 115 to said second cogwheel portion 124 and said third cogwheel portion 134. In order to impart torque and rotation motion to said first rod 112, a second handle 111 is arranged at the second end of said first rod 112. The fact that the first rod 112 is removable from said cannulation 144 has the advantage of allowing an easier cleaning and disinfection of said insertion instrument assembly 100.

Figure 9:
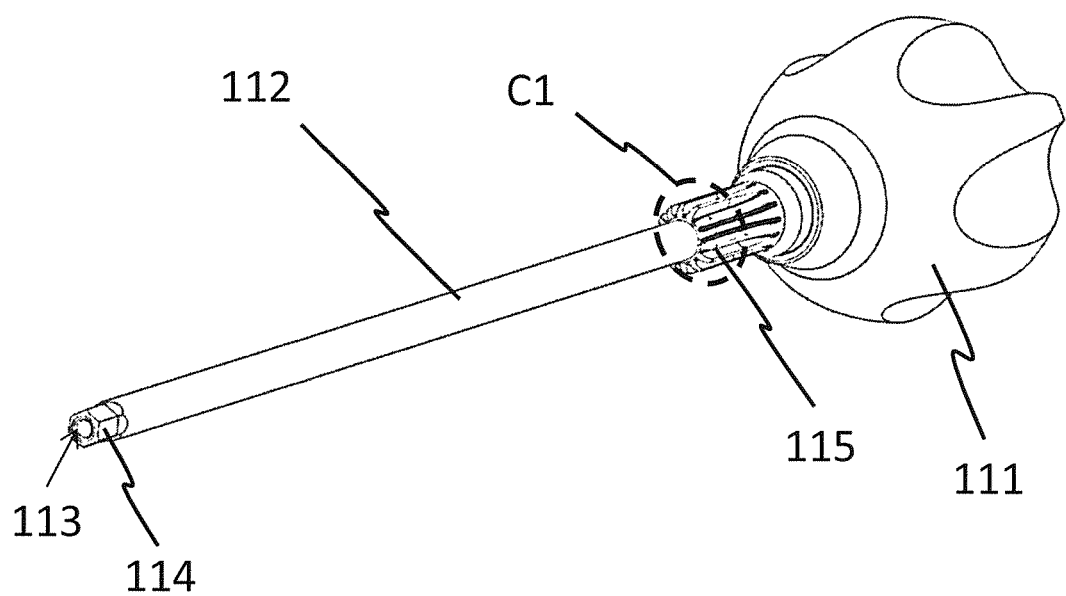
FIG. 9 a detailed representation of the first rod.

FIG. 9 shows a detailed view of the first rod 112 disassembled from the insertion instrument assembly 100. The first rod 112 comprises a second handle 111, a first cogwheel portion 115 with a first thread pitch circle circumference C1 at a second end as well as a first male drive 114 at a first end. The first rod 112 includes a cannulation 113 configured to slide over a guide wire, such as a K-wire.

Figure 10A:
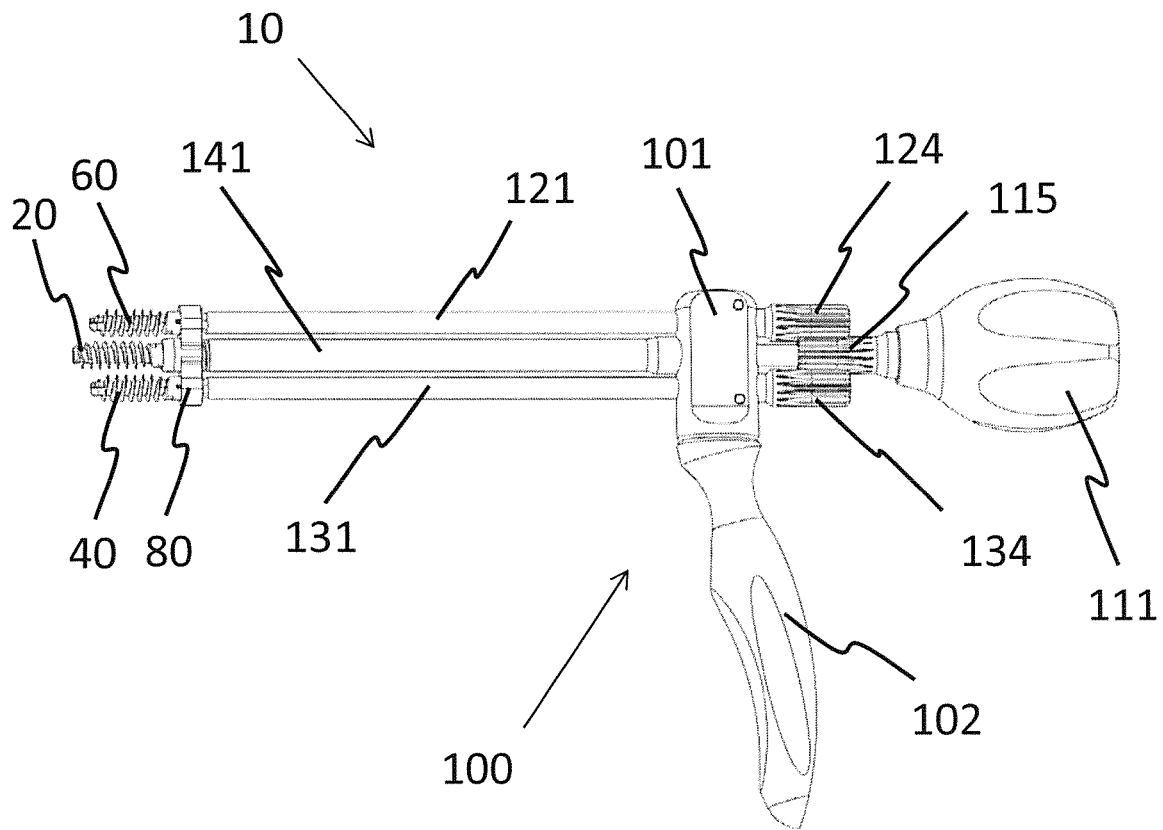
FIGS. 10a, 10b the inventive implant assembly with the insertion instrument assembly engaged with the implant body.
Figure 10B:
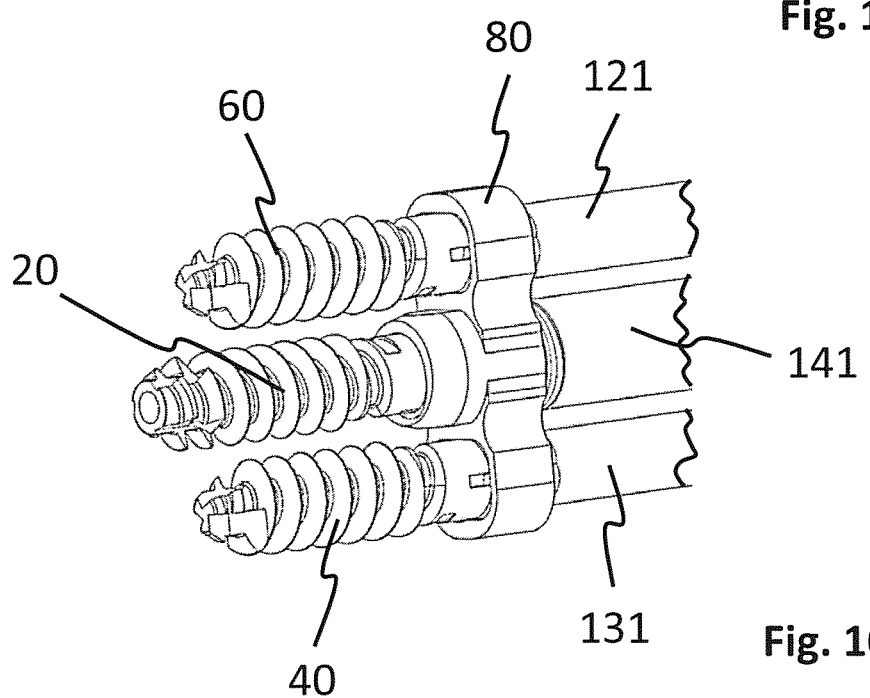

FIGS. 10*a* and 10*b* show the implant assembly 10 with the insertion instrument assembly 100 engaged with the implant body 80. The threaded end 142 of the cannulated shaft 141 is threadingly engaged with said internal thread feature 87 of said first aperture 83. The second male drive 122 of said second rod 121 is engaged with the second female drive 45 of the second screw 40. Likewise, the third male drive 132 of said third rod 131 is engaged with the third female drive 65 of the third screw 60. The first rod 112 is arranged within the cannulation 144 of the cannulated shaft 141, wherein the first male drive 114 is engaged with the first female drive 25 of the first screw 20.

The first cogwheel portion 115 of the first rod 112 meshes with said second cogwheel portion 124 of the second rod 121 as well as with the third cogwheel portion 134 of the third rod 131. As a result, rotation of the first rod 112 by means of the second handle 111, the second rod 121 and the third rod 131 are rotated as well. As each rod 112, 121, 131 is engaged with a screw 20, 40, 60 rotational motion is imparted onto the screws 20, 40, 60 as well. As the cogwheel portions 115, 124, 134 are directly meshing with each other, the second rod 121 and the third rod 131 have a direction of rotation which is opposite the direction of rotation of said first rod 112. I.e. when the first rod 112 is turned clockwise, the second rod 121 and the third rod 131 will rotate counter-clockwise.

To achieve a simultaneous advancement all three screws 20, 40, 60 into bone or a joint gap space the first screw 20 has a first handedness which is opposite a second handedness of said second screw 40 and said third screw 60. Furthermore, the ratio of all pitch circle circumferences C1, C2, C3 of said cogwheel portions 115, 124, 134 relative to each other are equal to the ratio of the lead lengths L1, L2, L3 relative to each other.

In an alternative embodiment, the cogwheel portions 115, 124, 134 do not directly mesh with each other, but mesh with at least one intermediate cogwheel. As a result all screws turn in the same direction, and therefore all screws have the same handedness.

FIGS. 11a to 11f show exemplary implantation steps for an implant system 10 according to FIGS. 10a and 10b. In a first step, shown in FIG. 11a, a Kirschner Wire 150 is inserted into the joint space 151 between the ilium bone 152 and the sacral bone 153 of a patient.

Figure 11A:
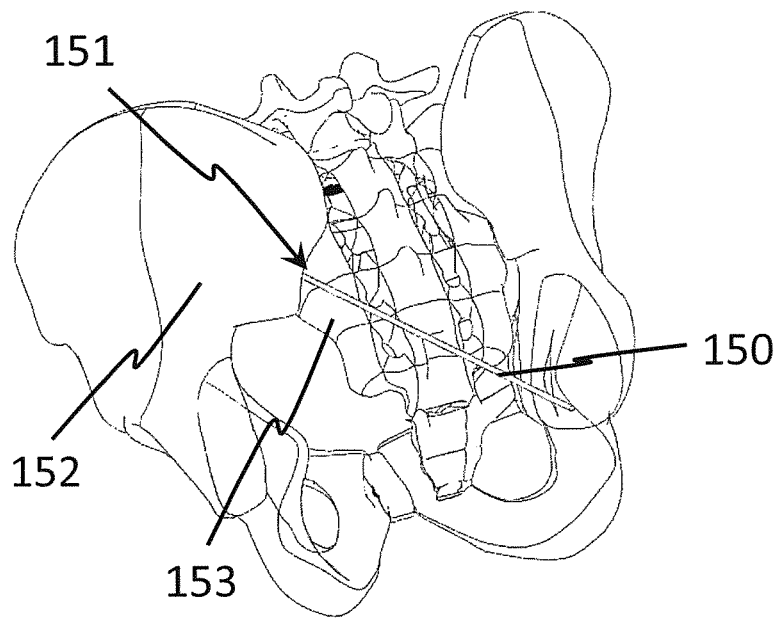
FIGS. 11a-11f exemplary implantation steps for an implant system according to FIGS. 10a, 10b.
Figure 11B:
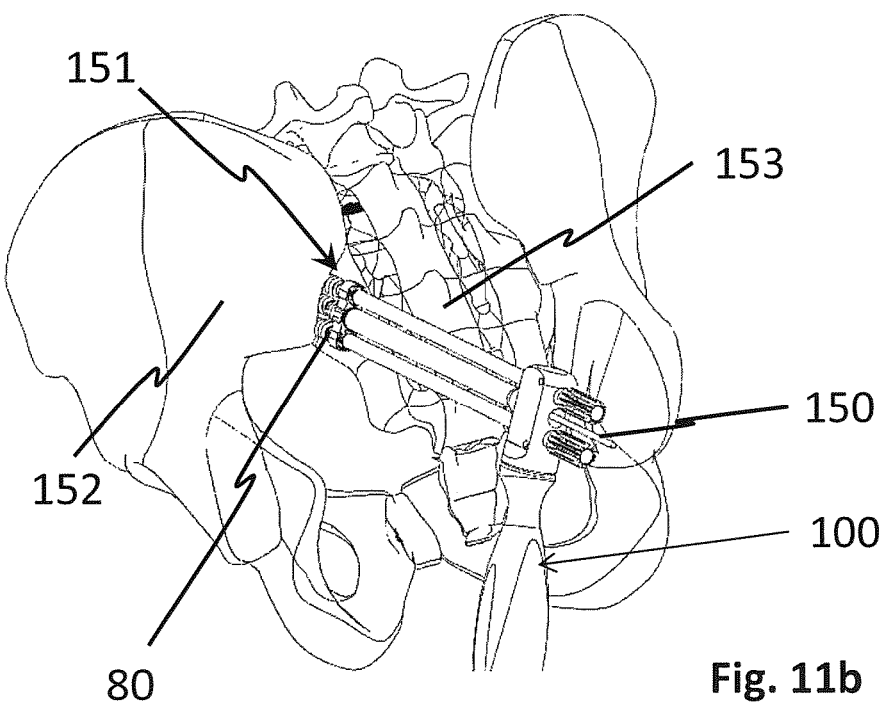

Then, as shown in FIG. 11b, an implant body 80 is arranged into the joint space 151 by means of an insertion instrument assembly 100 assembled therewith. The Kirschner Wire 150 is thereby inserted into the first central cannulation 27 of the first screw 20. Note that the first rod 112 is not yet arranged within the cannulated shaft 141. However, the Kirschner Wire 150 extends through said cannulated shaft 141.

Figure 11C:
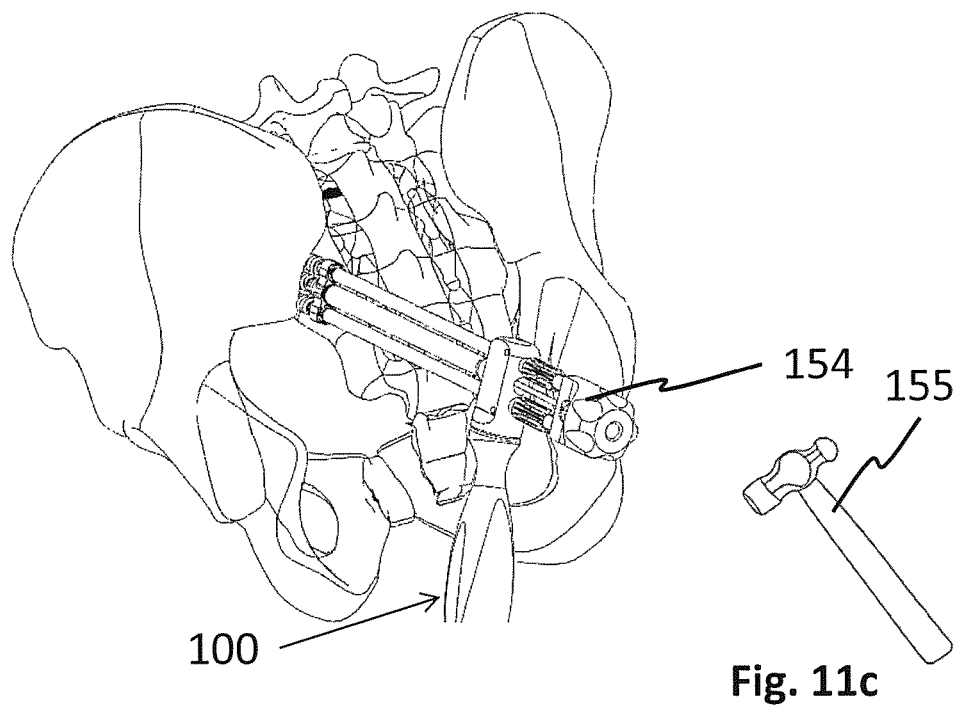

In a next step depicted in FIG. 11c the implant body 80 is pressed into the joint space 151. This may be done by using an impaction instrument 154 which is arranged into the cannulated shaft 141 and which may be subjected to tapping by means of an impaction tool 155.

Figure 11D:
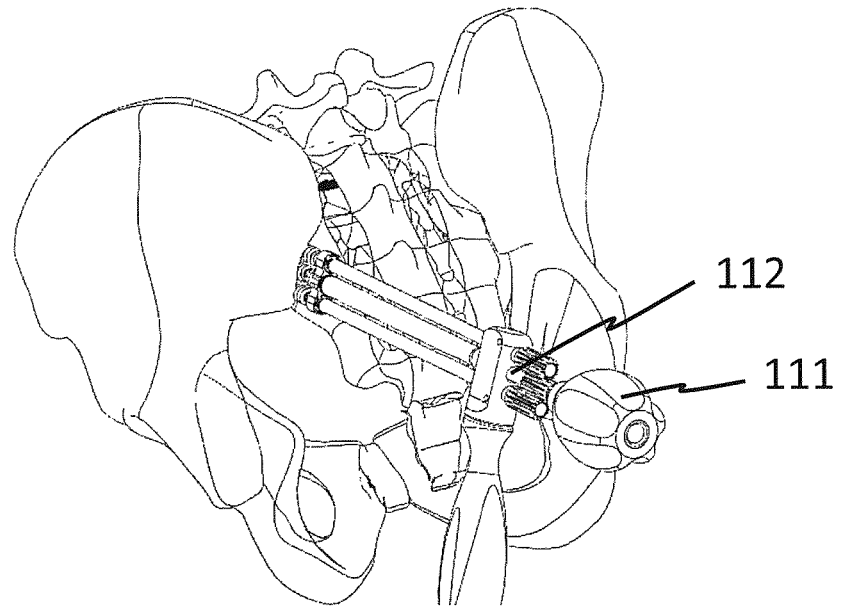

As shown in FIG. 11d, the first elongated rod 112 with the second handle 110 is then inserted into the cannulated shaft 141, wherein the first male drive 114 is brought into engagement with the first female drive 25 of the first screw 20.

Figure 11E:
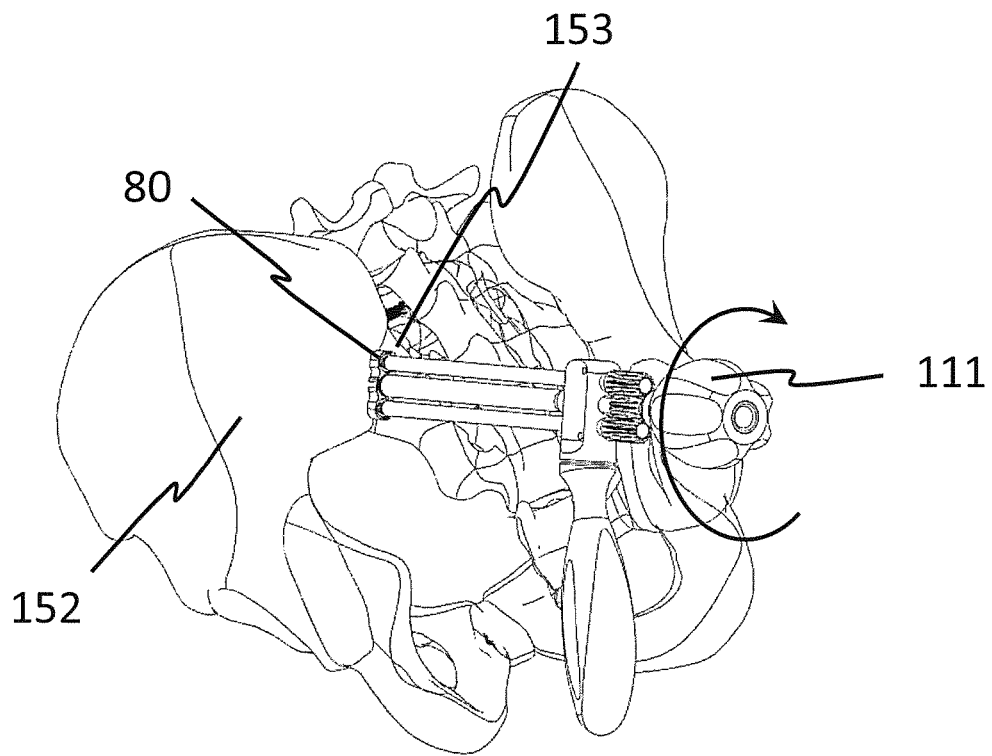

Finally, the second handle 111 is rotated, as shown in FIG. 11e. By rotating the second handle 111, rotational movement and torque is transmitted via the first rod 112 to the first screw 20.

Likewise, the meshing of the first cogwheel portion 115 with the second cogwheel portion 124 of the second rod 121 and with the third cogwheel portion 134 of the third rod 131 causes a transfer of rotational movement and torque to the second screw 40 and the third screw 60 via second rod 121 and third rod 131, respectively. Hence, the threaded elongated shafts 21, 41, 61 are advanced into the joint space 151. The threads of the threaded elongated shafts 21, 41, 61 will cut into the joint surfaces and prevent a back-out of the implant body 80. Furthermore, the cutting of the threads into bone material will create a bleeding which facilitates the bone growth and hence fusion of said ilium bone 152 with said sacral bone 153. The core diameters of the screws 20, 40, 60 will cause a distraction and therefore stabilize the joint space 151.

Figure 11F:
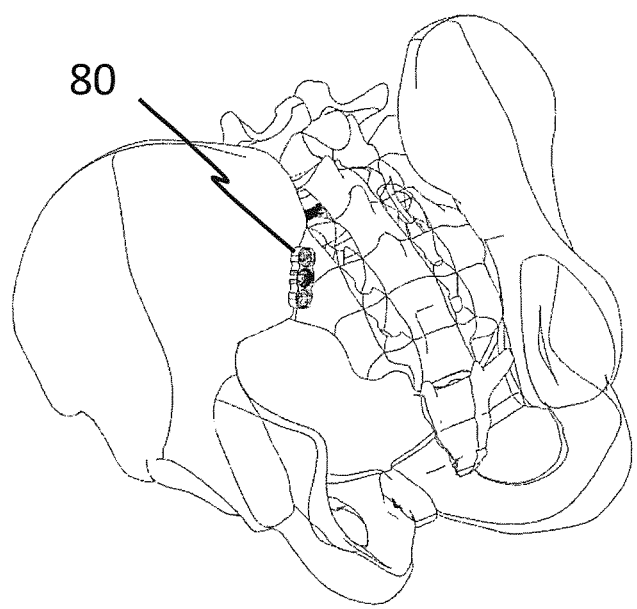

As shown in FIG. 11f, the insertion instrument assembly is subsequently disassembled from the implant body 80. Said implant body 80 and said screws 20, 40, 60 remain within the joint space 151.

Figure 12:
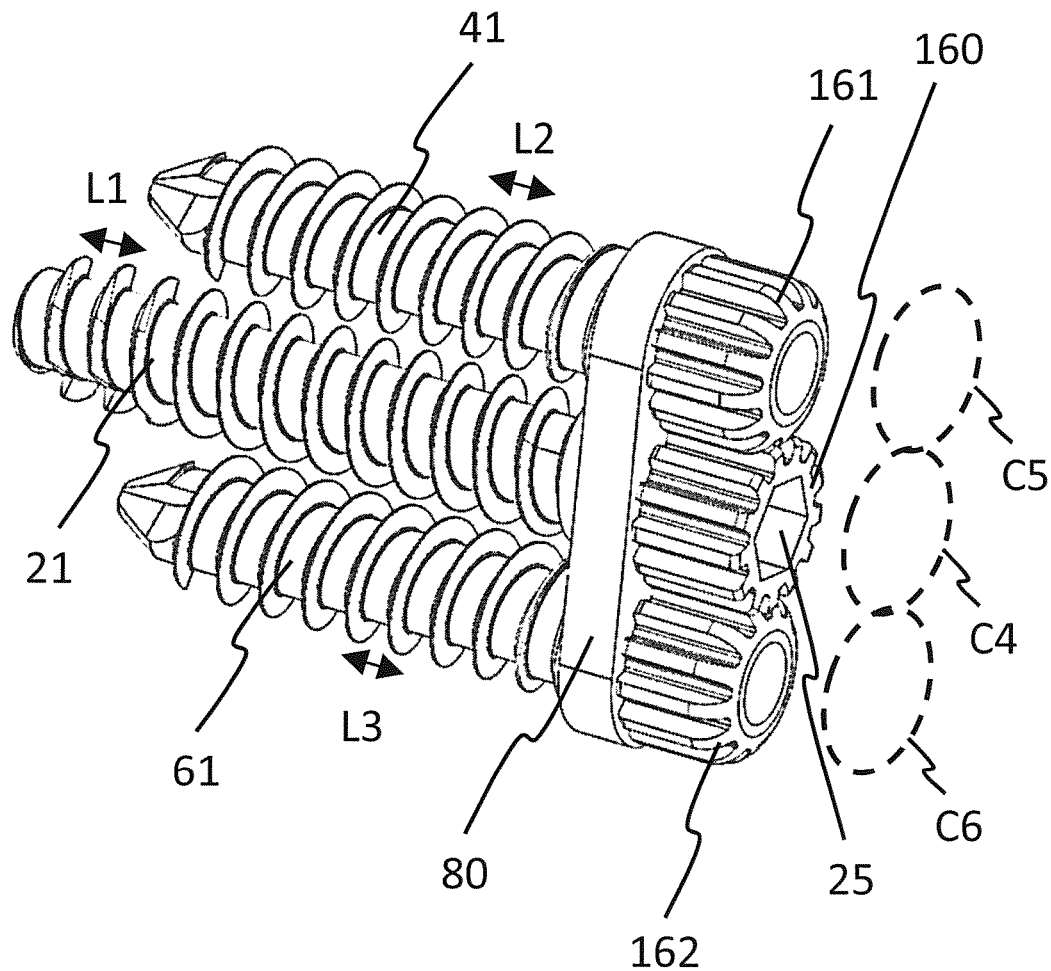
FIG. 12 an alternative embodiment of the screws with cogwheel heads.

FIG. 12 shows an alternative embodiment of the screws 20, 40, 60. Said screws 20, 40, 60 comprise cogwheel heads 160, 161, 162. The first cogwheel head 160 of said first screw 20 comprises a first female drive 25 which may be brought into engagement with the first male drive 114 of the insertion instrument assembly 100. The first cogwheel head 160 meshes with the second cogwheel head 161 and with the third cogwheel head 162 of the second screw 40 and the third screw 60, respectively. Said cogwheel heads 160, 161, 162 act as transmission means for rotational movement and torque. The cogwheel head 160, second cogwheel head 161 and third cogwheel head 162 have a fourth pitch circle C4, a fifth pitch circle C5 and a sixth pitch circle C6, respectively. Such as to allow a simultaneous advancement of all screws 20, 40, 60 into the joint space 151, the lead of the first screw 20 is of a first handedness while the lead of the second screw 40 and the third screw 60 is of a second handedness opposite said first handedness.

Further, the ratio of the pitch circles C4, C5, C6 of the cogwheel heads 160, 161, 162 relative to each other is equal to the ratio of the lead lengths L1, L2, L3 of the threaded elongated shafts 21, 41, 61 of the screws 20, 40, 60 relative to each other. Hence, L1:L2:L3 is equal to C4:C5:C6.

The invention claimed is:

1. An implant for implanting between joint surfaces of the joint space of a sacroiliac joint, comprising:
    an implant body with at least two apertures defining a respective central axis, the implant body comprising an insertion instrument assembly facing side, and a joint space facing side, wherein the implant further comprises:
    at least two screws, each with a screw head and a threaded elongated shaft, said at least two screws being rotatably engaged within said at least two apertures, and wherein said at least two screws protrude from the joint space facing side such that the threads of the elongated shafts are arranged for cutting into the joint surfaces when implanted in the joint space at least two screws, each with a screw head and a threaded elongated shaft, the at least two screws being rotatably engaged within the at least two apertures, wherein the at least two screws protrude from the joint space facing side such that the threads of the elongated shafts are arranged for cutting into the joint surfaces when implanted in the joint space by rotating the at least two screws, wherein the at least two apertures comprise a respective constriction element to prevent separation of a respective screw head from a respective socket of a respective aperture of the at least two apertures during implantation of the implant, and wherein at least one of the at least two screws is configured to swivel while being engaged in a respective socket of a respective aperture of the at least two apertures such that it is only allowed to swivel around one respective swivel axis while being rotatably engaged within the respective socket, the respective swivel axis being transverse to a respective central axis of the at least two apertures.

2. The implant according to claim 1, wherein the at least two apertures span from the insertion instrument assembly facing side to the joint space facing side.

3. The implant according to claim 1, wherein the screw heads are arranged to be held within the at least two apertures in a form-fitting manner.

4. The implant according to claim 1, wherein the insertion instrument assembly facing side is located opposite to the joint space facing side.

5. The implant according to claim 1, wherein the sockets have a spherical shape.

6. The implant according to claim 1, wherein the screw heads of the at least two screws each comprise a toothed circumference, the teeth of the toothed circumferences meshing with each other such that a rotational movement of one of the screws is transmitted to the at least one further screw.

7. The implant according to claim 6, wherein the ratio between a first thread lead of the threaded elongated shaft of a first screw and a second thread lead of the threaded elongated shaft of at least one further screw neighbouring the first screw is equal to the ratio between a first diameter of the toothed circumference of the first screw and a second diameter of the toothed circumference of the at least one further screw.

8. The implant according to claim 1, wherein a maximal swiveling angle relative to the respective central axis is in the range of 1° to 45°.

9. The implant according to claim 1, wherein the threaded elongated shaft of one of the at least two screws comprises a thread with a first handedness and in that the threaded elongated shaft of the further of the at least two screws comprises a thread with a second handedness being opposite of the first handedness.

10. An implant system comprising the implant according to claim 1, and further comprising:
    an insertion instrument assembly with a basis, a first holding means and at least one rotatable driving means configured for engagement with a drive of at least one of the at least two screws, wherein the at least two screws or the insertion instrument assembly comprises transmission means such that a rotational movement of a first screw of the at least two screws is transferred to the at least one further screw.

11. The implant system according to claim 10, wherein at least one aperture is configured to be releasably connected with the insertion instrument assembly.

12. The implant system according to claim 11, wherein the at least one aperture is configured to be releasably connected with the insertion instrument assembly by means of an internal thread feature arranged in the at least one aperture and being connectable to a threaded end of the insertion instrument assembly.

13. The implant system according to claim 12, wherein the threaded end is arranged on a cannulated shaft rotatably coupled to the basis, one rotatable driving means being releasably arranged within the cannulated shaft.

14. The implant system according to claim 10, wherein the insertion instrument assembly comprises one rotatable driving means for each of the at least two screws, wherein each of the rotatable driving means comprises a cogwheel shaped portion, the cogwheel shaped portions meshing with each other such as to transmit a rotational torque of one of the rotatable driving means to the at least one further rotatable driving means.

* * * * *